US008470335B2

United States Patent
Oh et al.

(10) Patent No.: US 8,470,335 B2
(45) Date of Patent: Jun. 25, 2013

(54) RECOMBINANT SARS-COV NSP12 AND THE USE OF THEREOF AND THE METHOD FOR PRODUCING IT

(75) Inventors: Jong Won Oh, Gyeonggi-do (KR); Dae Gyun Ahn, Gyeonggi-do (KR)

(73) Assignee: Industry-Academic Cooperation Foundation, Yonsei University Kookmin University Industry Academy Cooperation Foundation, Seoul (KR)

( * ) Notice: Subject to any disclaimer, the term of this patent is extended or adjusted under 35 U.S.C. 154(b) by 290 days.

(21) Appl. No.: 12/997,816

(22) PCT Filed: Jun. 13, 2008

(86) PCT No.: PCT/KR2008/003333
§ 371 (c)(1),
(2), (4) Date: Dec. 13, 2010

(87) PCT Pub. No.: WO2009/151165
PCT Pub. Date: Dec. 17, 2009

(65) Prior Publication Data
US 2011/0097730 A1    Apr. 28, 2011

(51) Int. Cl.
| | |
|---|---|
| C12N 15/50 | (2006.01) |
| C12N 15/33 | (2006.01) |
| C07K 16/00 | (2006.01) |
| C07K 16/10 | (2006.01) |
| A61K 39/00 | (2006.01) |
| A61K 39/12 | (2006.01) |
| A61K 39/215 | (2006.01) |
| C12P 21/06 | (2006.01) |
| C12Q 1/70 | (2006.01) |

(52) U.S. Cl.
USPC .................. 424/221.1; 424/185.1; 424/186.1; 424/192.1; 435/5; 435/69.1; 530/350

(58) Field of Classification Search
None
See application file for complete search history.

(56) References Cited

PUBLICATIONS

Zuo et al. Expression and purification of SARS coronavirus proteins using SUMO-fusions. Protein Expression and Purification 2005, vol. 42, pp. 100-110.*
Brunn et al. (2007) PLoS One, 2(5):e459. doi:10.1371/journal.pone. 0000459, "Analysis of Intraviral Protein-Protein Interactions of the SARS Coronavirus ORFeome".
Cheng et al. (2005) Virology 335:165-176, "Expression, purification, and characterization of SARS coronavirus RNA polymerase".
Imbert et al. (2006) The EMBO Journal 25:4933-4942, "A second, non-canonical RNA-dependent RNA polymerase in SARS Coronavirus".
Imbert et al. (2008) Virus Research 133:136-148, "The SARS-Coronavirus PLnc domain of nsp3 as a replication/transcription scaffolding protein".
International Search Report and Written Opinion, prepared by the Korean Intellectual Property Office, acting as International Searching Authority, for international patent application No. PCT/KR2008/003333, prepared Mar. 10, 2009, and mailed Mar. 11, 2009, 5 pages.

* cited by examiner

*Primary Examiner* — Louise Humphrey
(74) *Attorney, Agent, or Firm* — Swanson & Bratschun, LLC

(57) ABSTRACT

The present invention relates to a recombinant severe acute respiratory syndrome coronavirus (SARS-CoV) non-structural protein (nsp) 12 with an RNA polymerase activity, its expression vector, its preparation method, and its use. According to the present invention, a soluble recombinant SARS-CoV nsp12 with an RdRp activity of initiating SARS-CoV genome synthesis can be over-expressed in the transformed host cells, and conveniently purified with high purity. An in vitro replication system important for studying SARS-CoV replication can be established with the purified recombinant SARS-CoV nsp12. SARS-CoV nsp12 produced by the present invention can also be used as a target for the development of anti-viral agents against SARS-CoV. In addition, materials inhibiting RNA-dependent RNA polymerase (RdRp) activity of nsp12 can be screened efficiently according to the present invention as the optimal conditions for the RdRp assay with SARS-CoV nsp12 were found.

7 Claims, 13 Drawing Sheets

Figure 3:
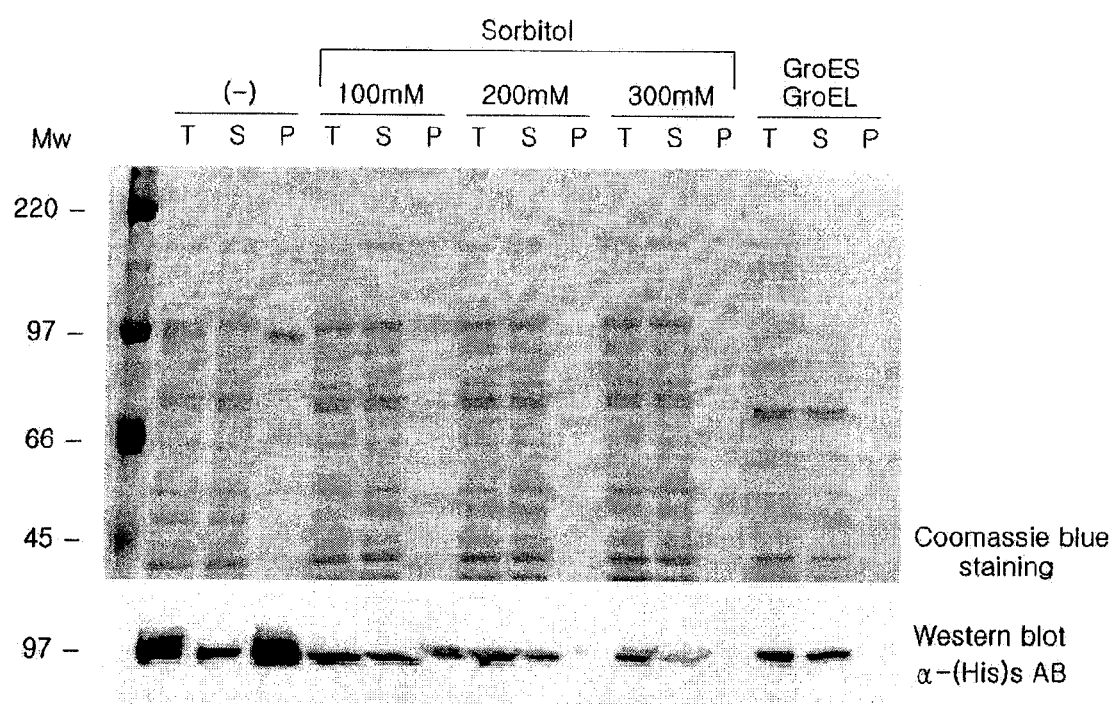
Figure 4:
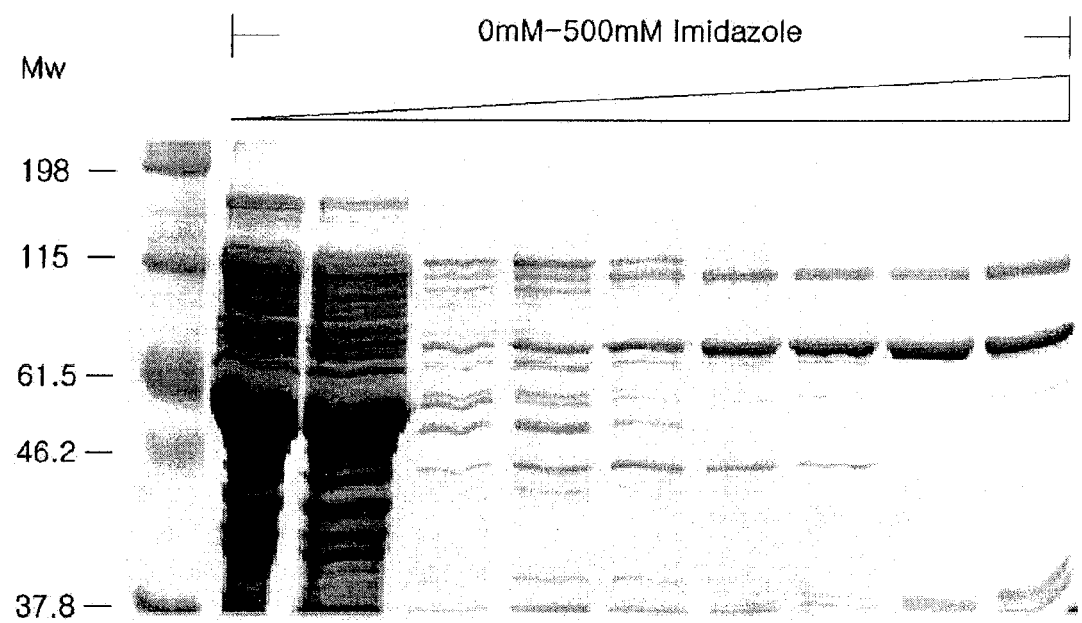
Figure 6:
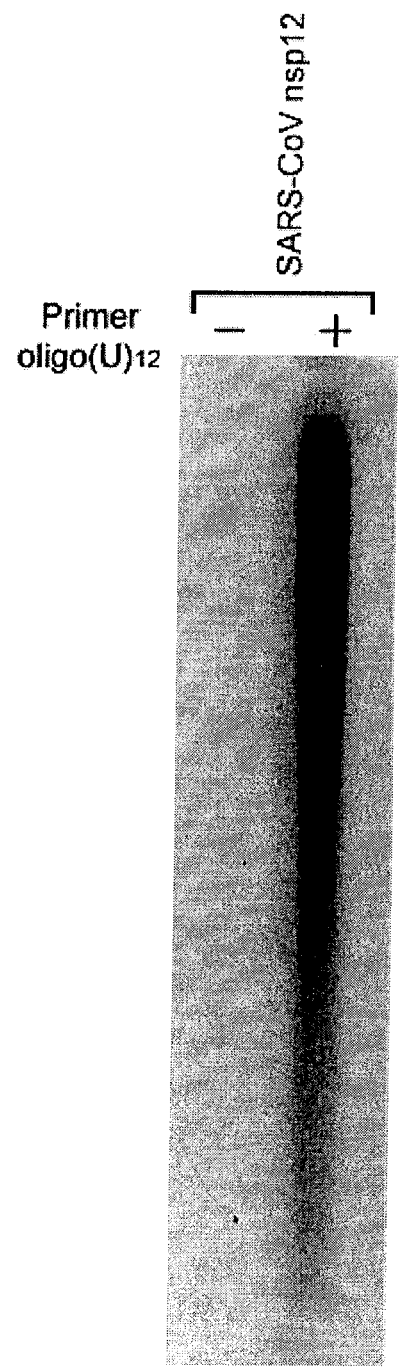
Figure 7:
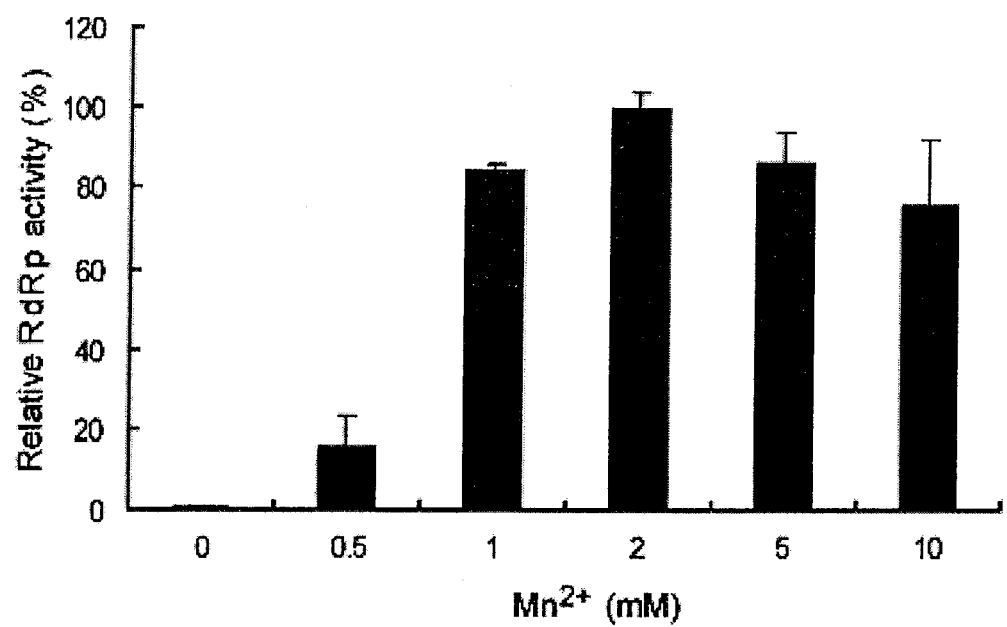
Figure 8:
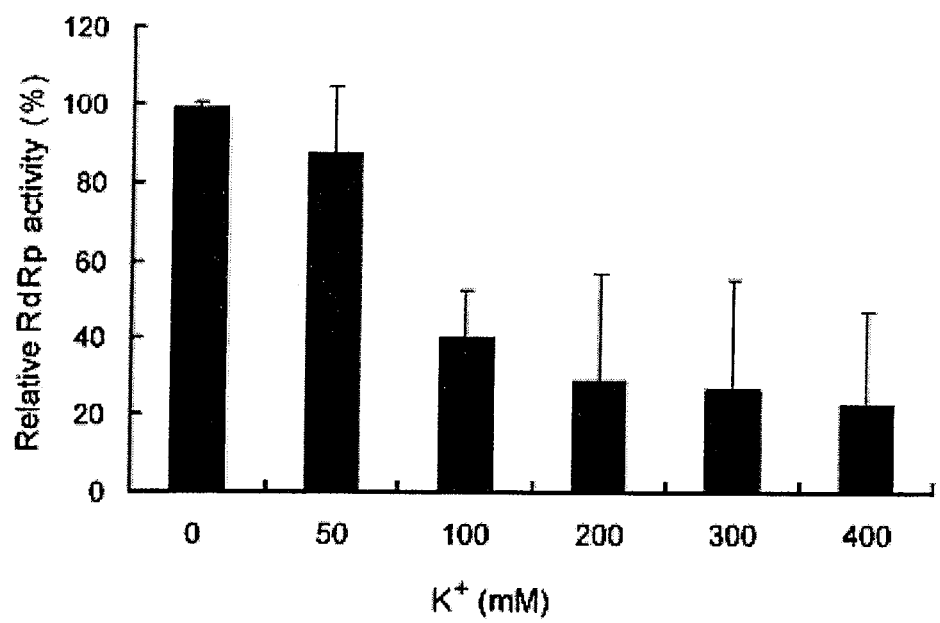
Figure 9:
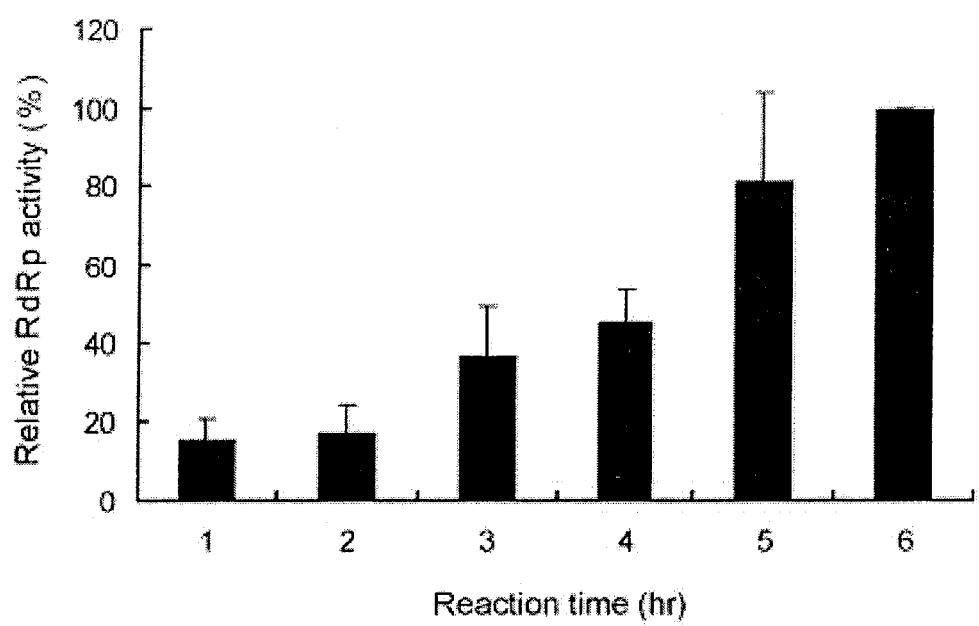
Figure 10:
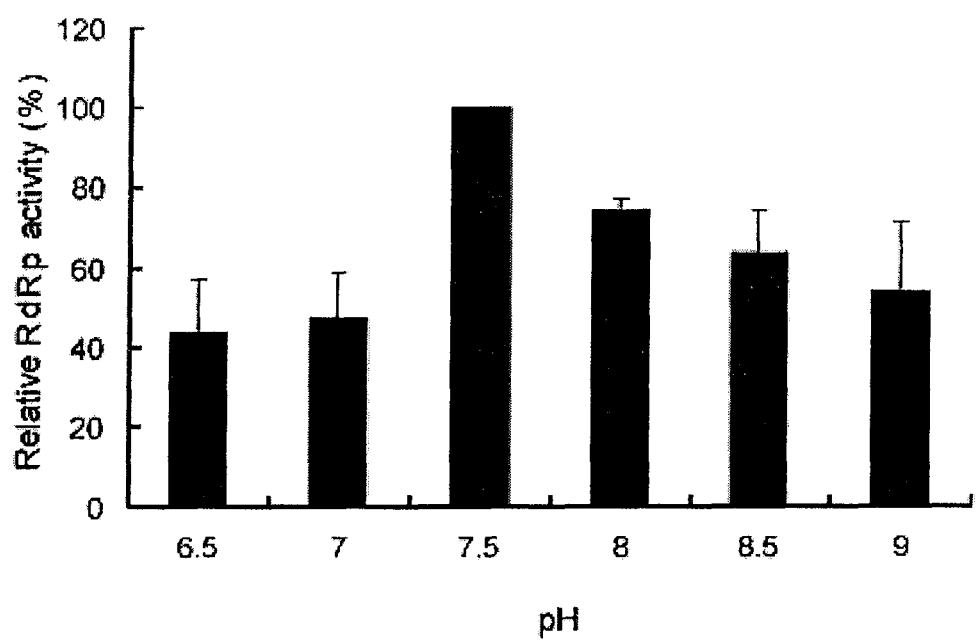
Figure 11:
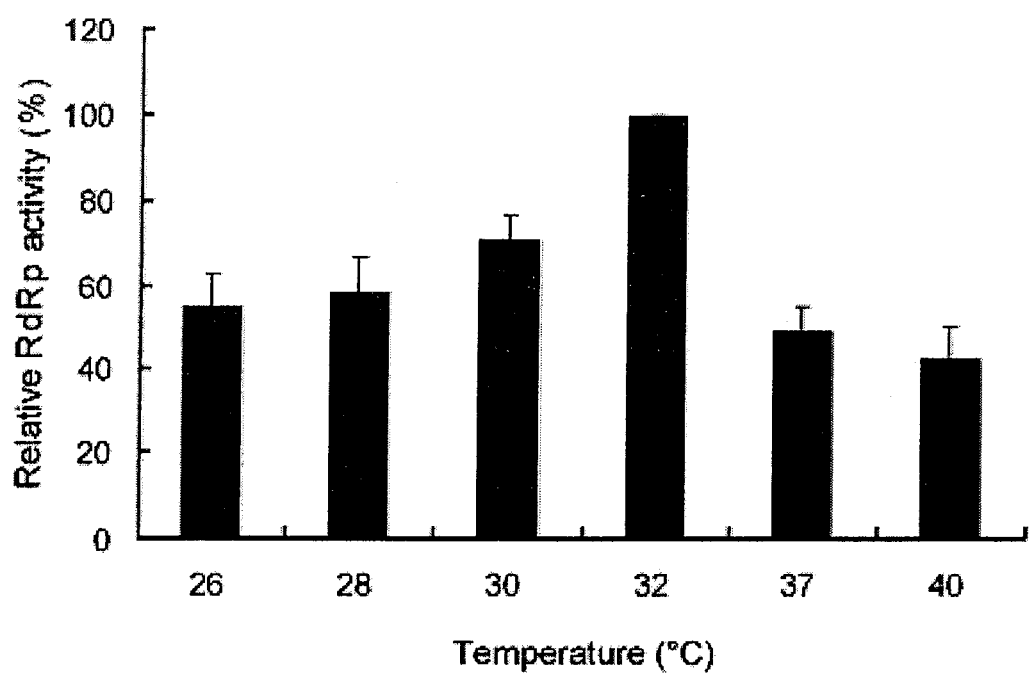

FIG. 1 trc promoter
RBS
Nco I(412)
6xHis-tag pTrcSARSnsp12
7122bp pBR322 origin

Amp

SARS-CoV nsp12

Eco RI(2643)

Bam HI(3224)
Eco RI(3261)
Hin dIII(3268)

Coomassie blue
staining

SARS-CoV nsp12

Western blot
α-(His)₅ AB

SARS-CoV nsp12

RECOMBINANT SARS-COV NSP12 AND THE USE OF THEREOF AND THE METHOD FOR PRODUCING IT

RELATED APPLICATIONS

This application is a 35 U.S.C. §371 national phase application of PCT/KR2008/003333 (WO 2009/151165 A1), filed on Jun. 13, 2008, entitled "Recombinant Sars-Cov nsp12 and the Use of Thereof and the Method for Producing it," which is incorporated herein by reference in its entirety.

TECHNICAL FIELD

The present invention relates to a recombinant severe acute respiratory syndrome coronavirus (SARS-CoV) non-structural protein (nsp) 12 with an RNA polymerase activity, its preparation method, and its use.

Incorporated by reference herein in its entirety is the Sequence Listing entitled "sequence list.txt," created Dec. 10, 2010, size of 21 kilobytes.

BACKGROUND ART

Since the first coronavirus infecting chickens was reported in 1937, about 15 coronaviruses belonging to the Coronaviridae family have so far been found to infect humans and animals including cattle, pigs, cats, dogs, birds, rodents, etc. Infections of animals like cattle, pigs, chickens, horses, etc. have major economical impacts on the animal husbandry industry. Particularly, porcine epidemic diarrhea, transmissible gastro-enteritis, and infectious bronchitis, caused by various animal coronaviruses, spread rapidly. Infection of infant animals is often associated with a high mortality rate. Currently, there are no effective therapeutic agents for coronavirus infection, which is economically damaging the animal husbandry industry. Regarding the coronaviruses infecting humans, human coronavirus is known to be responsible for 10-30% of all common colds in adults. SARS-CoV, emerged in the Guangdong province of China in November 2002, and spread to 26 countries worldwide including Hong Kong, Singapore, Vietnam, Canada, USA, etc. It became a worldwide health concern, with a significant impact on the economy as well. SARS is a respiratory disease caused by SARS-CoV, which is a coronavirus variant and is associated with symptoms such as fever, cough, respiratory distress, atypical pneumonia and the like. The latent period of SARS-CoV is about 2-7 days and 10-20% of patients suffer from acute respiratory distress syndrome with a death rate of 7-8%. According to World Health Organization (WHO) report in 2003, approximately 8,000 patients were found to be infected with SARS-CoV and approximately 770 of them died during the SARS outbreak in 2003. Except for several suspected SARS cases, additional infection has not been reported since April 2004. However, WHO and Center for Disease Control and Prevention (CDC) have been keeping a close watch on SARS as there are possibilities of re-emergence.

SARS-CoV belongs to the *Coronavirus* genus of the Coronaviridae family and has approximately 29.7 kb of positive-stranded RNA genome with cap-structure at 5'-end and poly (A) tail at 3'-end. SARS-CoV has 14 open reading frames (ORF) and 9 intergenic sequences flanked by 5' and 3' untranslated regions (UTRs) which are essential cis-acting elements for viral replication. A total of eight subgenomic RNAs are additionally transcribed from intergenic sequences to produce eight structural and accessory proteins. The ORF1 is composed of ORF1a and ORF1b, and the latter is translated by −1 ribosomal frameshift as a polyprotein, which is further processed by two viral proteases to generate a total of 28 viral proteins (Snijder et al., J. Mol. Biol. 331:991-1004).

It is known that RNA-dependent RNA polymerase (RdRp) plays a pivotal role in viral replication. The RdRp, probably with the help of various cellular proteins, initiates viral replication by recognizing cis-acting elements of viral RNA genome in infected cells. SARS-CoV nsp12 is encoded as a first protein in ORF1b and generated by processing of the above described polyprotein by 3C-like proteinase (nsp5). SARS-CoV nsp12 has the SDD motif that is common to coronavirus RdRps, suggesting that replication of SARS-CoV RNA genome might be mediated by nsp12 RdRp that is not present in human cells and is encoded by the viral genome.

In the absence of vaccines and therapeutic agents for various coronaviruses, development of functional RdRps is desperately needed to screen for inhibitors that can be used as antiviral agents. Moreover, antiviral drug screening in cell culture systems using a highly infectious SARS-CoV with a high mortality rate has various practical application limitations. Therefore, in vitro drug screening systems need to be developed. Indeed, tremendous efforts have been made to establish such systems using purified recombinant viral RdRps of SARS-CoV or other coronaviruses belonging to the *Coronavirus* genus and *Torovirus* genus in the Cornaviridae family. However, successful cases have not yet been reported. Even with the mouse hepatitis virus for which the coronavirus replication mechanism has been studied extensively since the 1980's, recombinant RdRp has not yet been developed and so in vitro RdRp assay systems have not been established. This is likely due to (1) low expression level of RdRp, (2) its insolubility when over-expressed, and (3) inability of purified RdRps to recognize and transcribe viral RNA templates. Recently, glutathione S-transferase-fused SARS-CoV RdRp (nsp12) was expressed and purified from *E. coli*. The recombinant protein was expressed mainly in insoluble form and cleaved into several fragments. Moreover, the authors did not demonstrate that the fusion RdRp protein, yet partially purified with its several cleaved forms, was able to copy RNA templates derived from the viral RNA genome (Cheng et al., Virology 335:165-176). Similarly, a purified recombinant RdRp of equine arteritis virus, which belongs to the *Arterivirus* genus in Nidovirale order, was not shown to be able to copy viral genome-derived RNA templates (Beerens et al., J. Virol. 81:8384-8395). In vitro replication systems for coronaviruses could be useful in studying viral RNA replication mechanisms, identifying target sites of antiviral agents by mapping of cis-acting elements, and screening for inhibitors against RdRp. Functional recombinant RdRp is the key element of the in vitro replication system. However, previous studies including the works described above have not yet established a robust in vitro replication system using a soluble, purified functional RdRp capable of utilizing the 3'-end RNA regions on both plus- and minus-strands of viral RNA, as templates.

DISCLOSURE

[Technical Problem]

The purpose of the present invention is to provide a recombinant SARS-CoV nsp12 capable of initiating SARS-CoV genome RNA synthesis.

Another purpose of the present invention is to provide an expression vector for expression of the recombinant SARS-CoV nsp12 in host cells.

One of the other purposes of the present invention is to provide a host cell transformed with the expression vector for expressing the recombinant SARS-CoV nsp12.

Yet another purpose of the present invention is to provide a method of preparing soluble recombinant SARS-CoV nsp12 efficiently.

Finally, the last purpose of the present invention is to provide the compositions and methods for screening inhibitors of SARS-CoV nsp12 RdRp.

[Technical Solution]

The present invention provides a recombinant SARS-CoV nsp12 protein in which nine amino acids are deleted from the N-terminus predicted by bioinformatics analysis, and amino acid sequences comprising several histidine residues are fused to the N-terminus.

The present invention provides an expression vector comprising a gene encoding the recombinant SARS-CoV nsp12.

The present invention provides a host cell transformed with the expression vector comprising the gene encoding the recombinant SARS-CoV nsp12.

The present invention provides a method of preparing the recombinant SARS-CoV nsp12 comprising:
  culturing cells transformed with an expression vector comprising the gene encoding SARS-CoV nsp12, in which nine amino acids are deleted from the N-terminus and amino acid sequences comprising several histidine residues are fused to the N-terminus;
  inducing the expression of SARS-CoV non-structural protein nsp12;
  lysing cultured transformed cells; and
  isolating and purifying SARS-CoV non-structural protein nsp12 from cell lysates. The present invention provides a composition for screening inhibitors against RNA-dependent RNA polymerase (RdRp), comprising SARS-CoV nsp12, $MnCl_2$, and NTP (nucleoside triphosphate).

The present invention provides a method of screening an inhibitor of RdRp, comprising the following steps:
  a) incubating a candidate compound with the above described composition for screening inhibitors against RNA-dependent RNA polymerase (RdRp); and
  b) determining whether the candidate promotes or inhibits an RNA synthesis activity of SARS-CoV nsp12.

The present invention is illustrated in more detail below.

The present invention provides a recombinant SARS-CoV nsp12 that lacks nine amino acids at the N-terminal encoded by the 3'-end region of the ORF1a upstream of the slippery sequence required for −1 frameshift, and amino acid sequences comprising several histidine residues are fused to the N-terminus.

SARS-CoV nsp12 is expected to have amino acid sequences at the N-terminus encoded by the ORF1a because of the programmed −1 frameshift induced by an RNA secondary structure, which is formed by the sequences derived from the junction region of two ORFs, namely ORF1a and ORF1b (Plant et al., PLoS Biol. 3:e172). In the present invention, the recombinant SARS-CoV nsp12 is produced by cloning of the gene starting downstream of the slippery sequence responsible for the −1 frameshift. The resulting protein thus lacks nine N-terminal amino acids (SADASTFFK) compared with the authentically processed nsp12 protein N-terminus. In addition, the protein is expressed as a fusion protein with several histidine residues at the N-terminus.

In the present invention, SARS-CoV nsp12 is fused to several histidine residues at the N-terminus for its convenient isolation and purification. The histidine-tag was used because it can be added by a simple cloning procedure, and it is unlikely to interfere with the activity of nsp12 and binds less cellular proteins due to its small size. The number of histidine residues fused at the N-terminus is not restricted if the tagged protein can be conveniently purified using purification columns without affecting enzyme activity of SARS-CoV nsp12. For example, 6-8 histidine residues may be added to the N-terminus of nsp12. In an embodiment of the present invention, the recombinant SARS-CoV nsp12 was produced as a fusion protein with six histidine residues at the N-terminus.

The amino acid sequences comprising several histidines may further comprises several extra amino acid sequences, in addition to the histidine-tag at the N-terminus of SARS-CoV nsp12. Such amino acid sequences can originate from an expression vector used for over-expression of the recombinant SARS-CoV nsp12 and are routinely introduced as extra sequences during cloning procedures. Thus, those extra amino acid sequences can be variable depending on the types of expression vectors, and as many as 2-10 amino acids can be introduced before or after the histidine-tag, which should not interfere with the activity of recombinant SARS-CoV nsp12.

In the following examples, an expression vector for expression of recombinant SARS-CoV nsp12 was constructed and recombinant nsp12 was expressed in *E. coli* under optimal conditions for the production of soluble nsp12. The soluble nsp12 protein was then purified by chromatography using various purification columns. In the present invention, the recombinant nsp12 to which a histidine tag is fused, allows convenient, rapid purification of the tagged protein. Enzymatic activity of the purified nsp12 was then measured using a poly(A) RNA template, and the ability of RNA synthesis initiation from SARS-CoV genome was assessed using the 3'(+)UTR RNA, which represents the 3'-UTR of positive strand viral RNA genome, and the 3'(−)UTR RNA, which represents the 3'-end region of negative strand viral RNA complementary to the 5'-UTR of positive strand genome. The assay results showed that the recombinant SARS-CoV nsp12 in the present invention has an RdRp activity useful for the establishment of an in vitro RNA replication system.

In the present invention, the recombinant SARS-CoV nsp12 can be expressed by a vector producing a functional RdRp that is able to copy the viral RNA and can be purified conveniently.

As such a vector, the present invention provides an expression vector comprising a gene encoding a recombinant SARS-CoV nsp12 in which nine amino acids are deleted from the N-terminus and amino acid sequences comprising several histidine residues are fused to the N-terminus.

In order to prepare the above expression vector, total RNA containing SARS-CoV (Urbani strain) genomic RNA is extracted from the virus-infected cells and the gene encoding the downstream of slippery sequence, lacking nine amino acids at the N-terminus of SARS-CoV nsp12 is obtained by RT-PCR. The PCR product is cloned into a well-known expression vector using restriction enzyme digestion. Such well-known expression vectors can be chosen depending on host cell types used for expression of the recombinant nsp12. For cloning of the nsp 12-coding gene, the gene can be manipulated to encode several histidine residues at the N-terminus of nsp12, Alternatively, expression vectors designed to encode several histidine residues at the N-terminus of target proteins can be used. These expression vectors include, for example, pQE vector (Qiagen), pET vector (Novagen), pRSET vector (Invitrogen), pTrc vector (Invitrogen), etc. An embodiment of the present invention provides the expression vector pTrcSARSnsp12 depicted in the restriction enzyme map shown in FIG. 1. In the pTrcSARSnsp12, the gene encoding the nsp12 and lacking the nine amino acid residues from the authentically processed N-terminal end of SARS-CoV nsp12 was inserted into pTrcHisB, a well-known expression vector designed to produce a fusion protein with several histidine residues at the N-terminus. As shown in FIG. 1, the above expression vector pTrcSARSnsp12 has the cDNA for the specified SARS-CoV nsp12 described above that was inserted into NheI/BamHI-cleaved pTrcHisB vector. To construct pTrcSARSnsp12, total RNA from SARS-CoV-infected cells is extracted and the gene encoding the above nsp12 is obtained by RT-PCR. Then, the product digested with restriction enzymes is inserted into the pTrcHisB vector to express a recombinant fusion protein with six histidine residues at the N-terminus. The expression vector pTrcSARSnsp12 enables the SARS-CoV nsp12 to be expressed in the fusion protein with six histidine residues at the N-terminus. SARS-CoV fused to histidine is conveniently purified by using a purification column capturing proteins with histidine residues.

Although pTrcSARSnsp12 was described as an example of an expression vector designed to express a $(His)_6$-tagged nsp12 in the present invention, any type of expression vector, which is designed to express the nsp12 with histidine residues as a tag for convenient purification, can be used.

The recombinant SARS-CoV nsp12 in the present invention includes the recombinant nsp12 expressed by pTrcSARSnsp12 shown in FIG. 1. The recombinant nsp12 expressed by the pTrcSARSnsp12 may have the amino acid sequence of SEQ ID NO: 1. The amino acid sequence of SEQ ID NO: 1 is obtained by deleting nine amino acids from the N-terminus of the amino acid sequence of SEQ ID NO: 2 that is an authentic full amino acid sequence, and fusing six histidine (indicated by bold letters) and extra amino acids (MGGSHHHHHHGMA) that are additionally inserted into the N-terminus during cloning procedures. The recombinant SARS-CoV nsp12 comprising SEQ ID NO: 1 sequence is only an example of the present invention, and the N-terminus amino acid sequences including histidine residues can be variable in terms of the sequence length of histidine residue and the compositions for the extra sequences introduced during cloning procedures.

The present invention provides a host cell transformed with an expression vector comprising the gene encoding SARS-CoV nsp12, in which nine amino acids are deleted from the N-terminus and amino acid sequences comprising several histidine residues are fused to the N-terminus. Any type of host cell, which can be cultivated easily and efficiently express recombinant proteins, can be used to produce the recombinant SARS-CoV nsp12. As examples of such a host cell, there are microorganisms such as bacteria and yeasts, insect cells, and animal cells. In an embodiment of the present invention, the host cell may be an *Escherichia coli* (*E. coli*) cell. In one example of the present invention, *E. coli* TOP10 cells were used as host cells for transformation with pTrcSARSnsp12, but host cells that can be used in the present invention are not limited to this particular *E. coli* strain. The present invention also provides a method of preparing a recombinant SARS-CoV nsp12 comprising: culturing cells transformed with an expression vector comprising the gene encoding SARS-CoV nsp12, in which nine amino acids are deleted from the N-terminus and amino acid sequences comprising several histidine residues are fused to the N-terminus; inducing the expression of SARS-CoV non-structural protein nsp12; lysing cultured transformed cells; and isolating and purifying SARS-CoV non-structural protein nsp12 from cell lysates.

The host cells transformed with the expression vector of the present invention are cultivated at the growth conditions and media optimal for each host. Induction conditions for expression of recombinant nsp12 can be variable depending on the expression modes of the expression vectors encoding the nsp12.

According to the present invention, osmotic stress or co-expression of chaperone proteins can enhances the production of soluble nsp12 during induction of nsp12 expression. Previous attempts to establish in vitro RNA replication systems have been unsuccessful for many RNA viruses due to very low expression level and low solubility of many viral RdRps when over-expressed. However, using the methods developed in the present invention, a higher amount of soluble nsp12 can be produced. As disclosed in the following experimental example, solubility of nsp12 was enhanced by the addition of bateine and/or sorbitol to trigger osmotic pressure or by co-expression of various chaperone proteins.

After induction of the nsp12 protein expression, host cells are lysed and the nsp12 is purified from cell lysates using the purification column capturing proteins with histidine residues.

Any kind of column for selectively capturing the proteins with histidine residues as a tag can be used for purification of the nsp12. A few examples of such columns include Ni-Sepharose, HisPur cobalt resin, Talon resin, etc. In one embodiment of the present invention, Ni-nitrilotriacetic acid (NTA)-Sepharose column recognizing histidine residues is used. Additional purification columns can be used to improve the purity of the nsp12. Such additional columns include, for example, ion-exchange columns, gel-filtration columns etc. As ion-exchange columns, Q-Sepharose, DEAE (diethylamino ethyl)-Sepharose, CM (carboxymethyl)-Sepharose, and SP (sulphopropyl)-Sepharose columns, for example, can be used. As gel filtration columns, Sephacryl-, Sephadex-, and Superpose-columns can be used. In one embodiment of the present invention, Q-Sepharose column can be used as an additional purification column.

Inventors of the present invention determined the optimal RdRp activity assay conditions for SARS-CoV nsp12 in the course of characterization of the activity of recombinant SARS-CoV nsp12. As disclosed in the following example, manganese ion is inevitable for optimal RdRp activity of SARS-CoV nsp12. The optimal conditions for RdRp assay using the nsp12 are of significant importance not only for establishment of in vitro RNA replication systems but also for screening for anti-viral agents against SARS-CoV nsp12 RdRp. More specifically, inhibitory effects of potential antiviral agents can be evaluated by assessing the level of RNA synthesized by the nsp12 in the presence of a candidate compound, under the optimized RdRp assay conditions. Thus, the present invention provides a composition for screening inhibitors against RdRp, comprising SARS-CoV nsp12, $MnCl_2$, and NTP (nucleoside triphosphate). The present invention also provides a method of screening an inhibitor of RdRp, comprising the following steps: a) incubating a candidate compound with the composition for screening an inhibitor of RdRp; and b) determining whether the candidate promotes or inhibits an RNA synthesis activity of SARS-CoV nsp12. In order to screen for inhibitors of the RdRp, the methods can assess whether a candidate compound promotes or inhibits an RNA synthesis activity of nsp12 by incubation of the above composition with a candidate compound in the optimal conditions of RdRp activity. Thus, nucleoside triphosphate (NTP) required for RNA synthesis and $MnCl_2$ essential for optimal RdRp activity can be comprised in the composition for screening for inhibitors against RdRp activity of SARS-CoV nsp12. In addition, RNA templates, primers, and buffers for RNA synthesis can be comprised in the composition for screening for an inhibitor of nsp12 RdRp. For convenient measurement of the level of RNA synthesis by SARS-CoV nsp12 in the presence of a candidate compound, NTPs can be labeled with markers. For example, such markers include fluorescence or luminescence materials or radioactive isotopes. In one embodiment of the present invention, NTPs can be ATP, GTP, CTP, and UTP, labeled with digoxigenin, biotin, or fluorescein, or their mixtures. In another embodiment of the present invention, NTPs can be ATP, GTP, CTP, and UTP, labeled with radioactive isotopes, or their mixtures. For example, RNA synthesis can be readily monitored by radiation measuring instruments detecting the radioactive NTPs. Thus, the present invention provides a method of screening for inhibitors of nsp12 RdRp, comprising incubating a candidate compound with the composition; and determining whether the candidate promotes or inhibits RNA synthesis activity of SARS-CoV nsp12 by measuring whether the RNA labeled with a marker nucleotide is synthesized or not.

According to the present invention, a high-throughput screening (HTS) system could be established for the screening of candidate compounds for inhibitors against SARS-CoV RdRp.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

[Advantageous Effects]

According to the present invention, a soluble recombinant SARS-CoV nsp12 with an RdRp activity of initiating SARS-CoV genome synthesis can be over-expressed in the transformed host cells, and conveniently purified with high purity. An in vitro replication system important for studying SARS-CoV replication can be established with the purified recombinant SARS-CoV nsp12. SARS-CoV nsp12 produced by the present invention can also be used as a target for the development of anti-viral agents against SARS-CoV. In addition, materials inhibiting RdRp activity of nsp12 can be screened efficiently according to the present invention as the optimal conditions for the RdRp assay with SARS-CoV nsp12 were found.

DESCRIPTION OF DRAWINGS

FIG. 1 is a schematic diagram of the structure of recombinant nsp12 expression vector pTrcSARSnsp12 constructed in the present invention.

Figure 2:
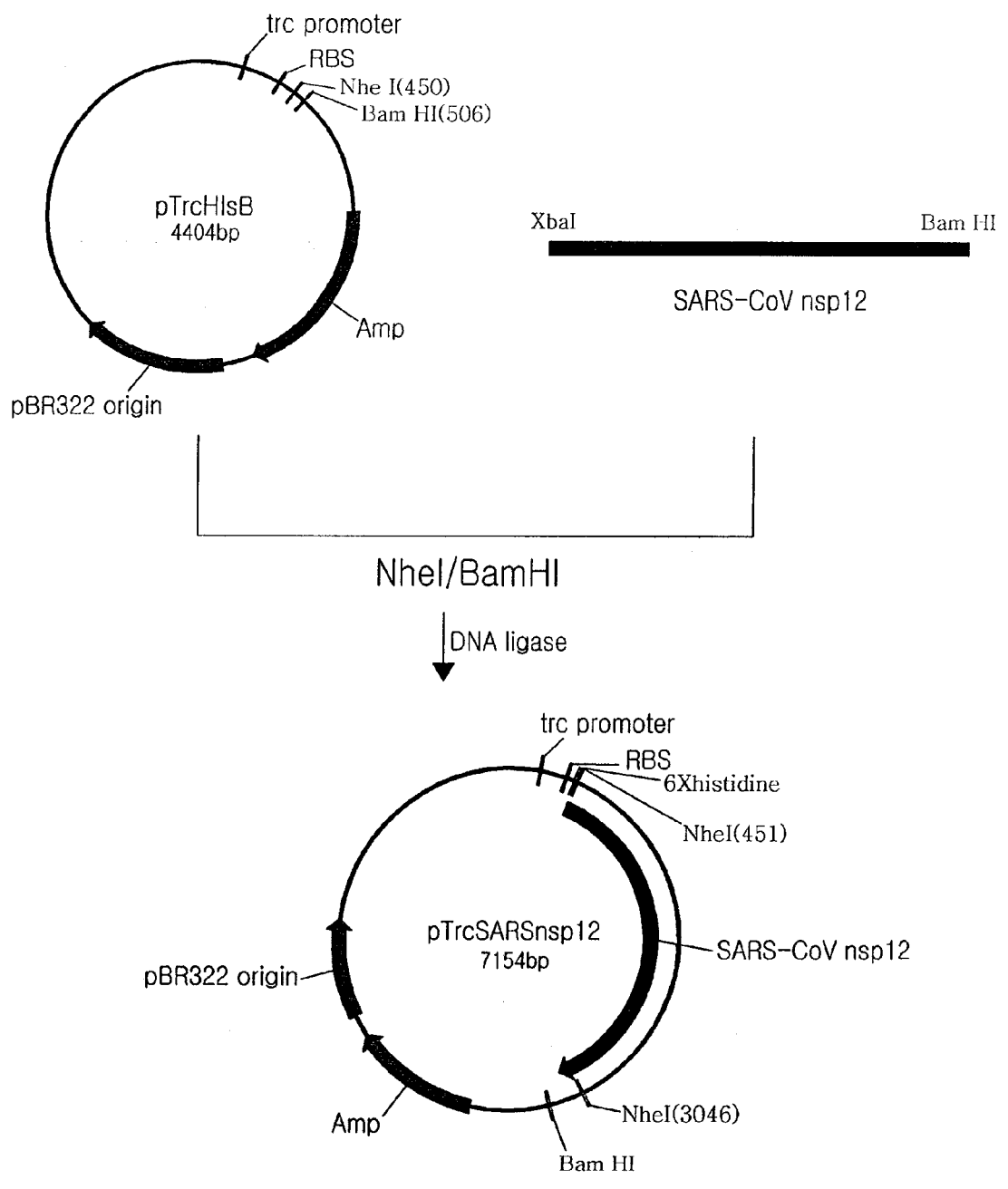

FIG. 2 is a schematic diagram of the construction procedures of pTrcSARSnsp12 vector.

FIG. 3 shows the results of Coomassie blue staining of SDS-PAGE gel (top panel) and Western blot analysis with anti-$(His)_5$ antibody (bottom panel). Total cell lysate (T), soluble supernatant fraction (S), and pellet fraction (P) of cell lysates of *E. coli* TOP10 cells, which were transformed with pTrcSARSnsp12 and grown with various concentrations of sortitol, or TOP10 cells, which co-express GroES/GroEL chaeperones, were resolved by SDS-PAGE. The (–) symbol indicates the samples from the *E. coli* transformants that were not treated with sortitol and were not co-transformed with a vector expressing GroES/GroEL chaeperones.

FIG. 4 shows the results of electrophoresis of the fractions eluted by gradient concentrations of imidazole (0 to 500 mM) for the purification of SARS-CoV nsp12.

FIG. 5 shows the results of electrophoresis of the purified SARS-CoV nsp12 resolved by SDS-PAG (left panel) or Western blot analysis using anti-$(His)_5$ antibody (right panel).

FIG. 6 shows the result of an RdRp activity assay performed with poly(A) RNA template using the purified SARS-CoV nsp12 in the absence (–) or presence (+) of oligo$(U)_{12}$ primer.

FIG. 7 shows the effect of manganese ion on the purified SARS-CoV nsp12 activity.

FIG. 8 shows the effect of potassium ion on the purified SARS-CoV nsp12 activity.

FIG. 9 shows the time course of RdRp reaction by the purified SARS-CoV nsp12 activity.

FIG. 10 shows the effect of pH on the purified SARS-CoV nsp12 activity.

FIG. 11 shows the effect of temperature on the purified SARS-CoV nsp12 activity.

FIG. 12 shows the results of RdRp assay of SARS-CoV nsp12 performed with SARS-CoV genome-derived RNA template and poly(A) tail function analysis.

FIG. 13 shows the results of RdRp assays with (+)3'UTR151ΔA and (–)3'UTR121 RNA templates, which are derived from SARS-CoV genome.

MODE FOR INVENTION

EXAMPLES

Example 1

Construction of the Recombinant SARS-CoV nsp12 Expression Vector

In order to obtain SARS-CoV nsp12 with RdRp activity, SARS-CoV RNA was isolated from SARS-CoV-infected cells (FDA) by the following method, thereby preparing a cDNA fragment encoding SARS-CoV nsp12. Total RNA including viral genomic RNA was extracted from SARS-CoV-infected cells using Trizol LS reagent (Invitrogen Life Technologies). Extracted RNA was precipitated with phenol/chloroform and isopropanol successively, washed once with 70% ethanol, and dissolved in RNase-free water. The RNA was reverse-transcribed using ImProm-II Reverse Transcription System (Promega) and R1 primer, thereby synthesizing cDNA. RNA and R1 primer were incubated for 5 min at 70° C. and chilled quickly on ice. The mixtures were incubated with reverse transcription buffer, 1 mM dNTP, and 20 U of ImProm-II reverse transcriptase (Promega) at 42° C. for 60 min. After reverse-transcription, enzymes were inactivated by incubation at 70° C. for 15 min.

The reverse-transcribed cDNA having the nucleic acid sequence of SEQ ID NO:3 was amplified by polymerase chain reaction (PCR) using F1 and R1 primers with the following conditions: total 25 cycles of 94° C. for 30 sec, 55° C. for 30 sec, and 72° C. for 3 min. The PCR product was digested with XbaI and BamHI and ligated into the pTrcHisB (Invitrogen) vector digested with NheI and BamHI to construct the plasmid pTrcSARSnsp12 (about 7 kbp) encoding the nsp12 with a $(His)_6$-tag at N-terminus (FIG. 1).

(SEQ ID NO: 4)
F1 primer: 5'-GCTCTAGAGTTTGCGGTGTAAGTGCAGC-3'

(SEQ ID NO: 5)
R1 primer: 5'-CGGGATCCTACTGCAAGACTGTATGTGG-3' cDNA for SARS-CoV nsp12 inserted in the recombinant expression vector pTrcSARSnsp12 has been cloned to comprise downstream of the slippery sequence where the programmed −1 ribosomal frameshift occurs. Therefore, the recombinant SARS-CoV nsp12 has the amino acid sequence of SEQ ID NO: 1 which is obtained by deleting nine amino acids (SADASTFFK) from the N-terminus of the amino acid sequence of SEQ ID NO: 2 that is an authentic full amino acid sequence, and fusing the amino acid sequence comprising six histidine (MGGSHHHHHHGMA)

Example 2

Improvement of the Solubility of Recombinant SARS-CoV nsp12 Protein

Like the other coronavirus RdRps, SARS-CoV nsp12 is mainly expressed as inclusion bodies, instead of soluble forms, causing difficulty in purification. In the present invention, the solubility of recombinant nsp12 was enhanced by induction of osmotic stress with betaine or sorbitol or by co-expression of chaperone proteins assisting the folding of protein tertiary structures. SARS-CoV nsp12 was over-expressed by cultivating *E. coli* cells transformed with pTrcSARSnsp12, in LB broth containing betaine or sorbitol or by cultivating *E. coli* cells co-transformed with pTrcSARSnsp12 and a vector expressing a chaperone protein(s). DnaK, DnaJ, GrpE, GroES, GroEL, TF etc. could be used as chaperone proteins. The solubility of recombinant SARS-CoV nsp12 expressed under different conditions described above was assessed by Coomassie blue staining of the SDS-polyacrylamide gel and Western blot analysis. After sonication of the cells over-expressing the nsp12, total cell lysate (T), supernatant fraction (S), and pellet fraction (P) were resolved by SDS-polyacrylamide gel electrophoresis, and subjected to Coomassie blue staining and Western blot analysis. As shown in FIG. 3, addition of sorbitol or co-transformation with GroES/GroEL significantly enhanced the level of soluble form nsp12 protein (FIG. 3.)

Example 3

Purification of Recombinant SARS-CoV nsp12 Protein from *E. Coli*

SARS-CoV nsp12 protein was expressed in *E. coli* TOP10 cells (Invitrogen) transformed with pTrcSARSnsp12. The cells were harvested by centrifugation (at 8,000 rpm) and washed twice with phosphate-buffered saline (pH 7.4, PBS) and resuspended in buffer A (50 mM Na-phosphate [pH 8.0], 300 mM NaCl, 10 mM imidazole, 10 mM β-mercaptoethanol, 10% glycerol, 1% Nonidet P-40) and frozen at −80° C. After thawing, the cells were lysed through ultrasonic lysis in an ice bath. The cell lysate was centrifuged for 20 min at 15,000 rpm to obtain clear lysate. The SARS-CoV nsp12 protein was purified by metal affinity chromatography using Ni-nitrilotriacetic acid (NTA)-Sepharose (Qiagen) resin equilibrated with the above buffer A. Unbound proteins were removed by washing the resin with 20 column volume of buffer A. The bound SARS-CoV nsp12 proteins were step-eluted with 10 ml of buffer A containing 20 to 500 mM imidazole. SARS-CoV nsp12-containing fractions were collected and purified proteins were resolved on SDS-PAGE gels (FIG. 4).

For further purification, collected fractions were transferred to a Q-Sepharose column (Amersham Biosciences) equilibrated with buffer B (50 mM Tris-HCl [pH 7.5], 50 mM NaCl, 1 mM DTT, 10% glycerol). Unbound proteins were removed by washing the resin with 20-column volumes of buffer B. Adsorbed proteins were eluted with buffer B having a linear gradient of NaCl from 0.1 to 1 M. SARS-CoV nsp12-containing fractions were collected, then proteins were resolved on SDS-PAGE gels and analyzed by Western blot (FIG. 5).

Example 4

Enzymatic Assays and Analysis of Products

Enzymatic activity of nsp12 purified as in Example 3 was measured by analysis of radioisotope-labeled RNA products subjected to denaturing polyacrylamide gel electrophoresis. Initial activity assay was performed in an RdRp assay buffer, described previously (Oh et al., J. Virol. 73:7694-7702), with 2 mM $MnCl_2$. After confirmation of the enzymatic activity of nsp12, optimal reaction conditions were established as in Example 5 and used for further characterization of the nsp12 in Example 4. RdRp assays were performed with 500 ng of purified SARS-CoV RdRp in a total volume of 25 μl containing 50 mM Tris-HCl (pH 7.5), 50 mM NaCl, 2 mM $MnCl_2$, 1 mM DTT, 10% glycerol, 20 units of RNase inhibitor (Promega), 1 μg of poly(A) template, 10 pmole of $oligo(U)_{20}$ and 3 μCi of [$\alpha$-$^{32}$P] UTP (3,000 Ci/mmol; Amersham Biosciences). The reaction mixture was incubated for 2 hr at 32° C. After reactions, 35 μl of distilled water containing 20 μg of glycogen (Roche) and 60 μl of an acidic phenol emulsion (phenol, chloroform, 10% SDS, 0.5 M EDTA [1:1:0.2:0.4]) were added to the reaction mixture to stop the reactions. After centrifugation, RNAs in supernatant were precipitated with 5 M ammonium acetate-isopropanol (1:5), washed with 70% cold ethanol and air-dried. RdRp reaction products were resuspended in a denaturing loading buffer (95% formamide, 10 mM EDTA, 0.025% each of xylene cyanol and bromopheonol blue). After heat denaturation and quick chilling on ice, the RNA products were resolved on 8 M urea-5% polyacrylamide gels. The dried gels were exposed to X-ray film (BioMax. XAR, Kodak) for autoradiography (Oh et al., J. Virol. 73:7694-7702).

The results demonstrate that the purified SARS-CoV nsp12 incorporated radioactivity to the RNA products only when the primer is present, indicating the primer-dependent RNA synthesis (FIG. 6).

Example 5

Optimization of Enzymatic Assay for SARS-CoV nsp12

Optimal RdRp activity assay conditions for the nsp12 were determined using the poly(A) RNA template and biotin-labeled $oligo(U)_{12}$ primer as described in Example 4. Optimal manganese ion ($Mn^{2+}$) concentration, potassium ion ($K^+$) concentration, reaction time, temperature, and pH for RdRp activity of nsp12 were determined. RdRp assays were performed with 500 ng of purified SARS-CoV RdRp in a total volume of 50 μl containing 50 mM Tris-HCl (pH 7.5), 50 mM NaCl, 2 mM $MnCl_2$, 1 mM DTT, 10% glycerol, 20 units of RNase inhibitor (Promega), 1 μg of poly(A) template, 10 pmole of biotin-labeled $oligo(U)_{12}$ and 3 μCi of [$\alpha$-$^{32}$P] UTP (3,000 Ci/mmol; Amersham Biosciences). The reaction mixture was incubated for 2 hr at 32° C. on a streptavidin-coated Flashplate (PerkinElmer Life Sciences). After reaction, the plate was washed twice with PBS and cpm (count per minute) of isotopes incorporated into synthesized RNA was measured by Top Counter (PerkinElmer Life Sciences). The results shown in FIGS. 7-11 demonstrate that the optimal RdRp activity was observed with 2 mM $MnCl_2$ and at a temperature of 30-34° C. and pH of 7-8.

Example 6

SARS-CoV Genome-Derived SARS-CoV 3'(+)UTR RNA Template Preparation

The 3'(+)UTR RNA, which was used as a SARS-CoV genome-derived RNA template for RdRp activity test in Example 7, was prepared by in vitro transcription using T7 RNA polymerase. SARS-CoV genomic RNA obtained as described in Example 1 was reverse-transcribed using the R3 primer. The resulting cDNA was used to obtain the 3'(+)UTR DNA template flanking 17 adenosines by PCR (total 25 cycles of 94° C. for 30 sec, 55° C. for 30 sec, 72° C. for 1 min) with the F3 and R3 primers. Similarly, 3'(+)UTR DNA template lacking the adenosine tail was also amplified by PCR using the F3 and R4 primers. These PCR products were inserted into pCR2.1-TOPO vector (Invitrogen) to construct pTOPO 3'(+)UTR-1 and pTOPO 3'(+)UTR-2 clones. After removal of T7 RNA polymerase promoter region from the pTOPO 3'(+)UTR-1 and pTOPO 3'(+)UTR-2 by restriction enzyme XhoI and BglII treatment, PCR was performed with a set of primers described above. RNA templates for RdRp assay were generated using BsaI-treated PCR DNA templates by in vitro transcription using the T7 Megascript kit (Promega). After in vitro transcription, DNA templates were removed by treatment with DNase (Ambion) at 37° C. for 30 min. RNA transcripts were extracted by phenol/chloroform (Sigma) and precipitated using isopropyl alcohol. The concentration of purified RNA templates was estimated by measuring the absorbance at 260 nm. In vitro transcribed RNAs from the PCR product obtained from pTOPO 3'(+)UTR-1 as described above has 339 nucleotides of SARS-CoV genome 3'-UTR with 17 adenosines and thus named 3'(+)UTR339+17A. In vitro transcribed RNAs from the PCR products obtained from pTOPO 3'(+)UTR-2 has only 339 nucleotides of SARS-CoV genome 3'-UTR lacking the poly(A) tail and thus named 3'(+)UTR339ΔA.

F3 primer:

(SEQ ID NO: 6)
5'-<u>TAATACGACTCACTATAGG</u> ACACTCATGATGACCACAC-3'

(SEQ ID NO: 7)
R3 primer: 5'-GGTCTCTTTTTTTTTTTTTTTTT-3'

(SEQ ID NO: 8)
R4 primer: 5'-GTCCATTCTCCTAAGAAGCTA-3'

In the above primers, the underlined nucleotides are a T7 promoter sequence for transcription, and complimentary sequences to SARS-CoV genome are indicated in bold, capital letters.

Example 7

Figure 12:
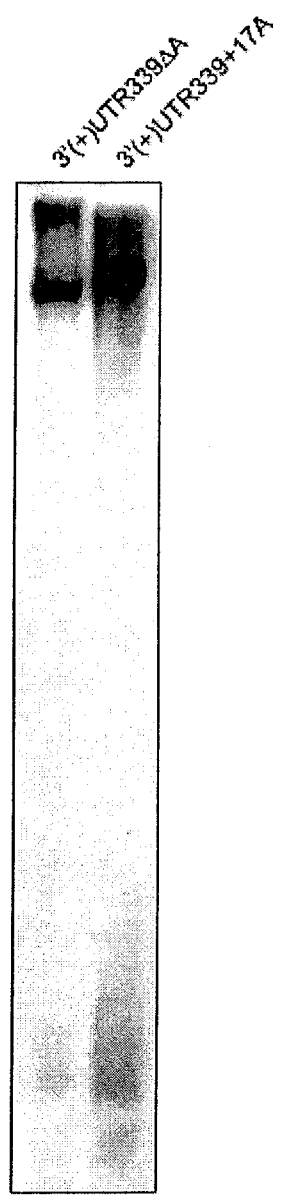

Analysis of RdRp Activity SARS-CoV nsp12 on SARS-CoV Genome-derived RNA Templates and Function of Poly(A)-tail on RNA Synthesis RdRp activity assay for the nsp12 purified as described in Example 3 and analysis of poly(A)-tail function were performed by measuring the amount of incorporated radioactive ribonucleotides in RNA products. More specifically, the RdRp assays were performed with 500 ng of purified SARS-CoV nsp12 in a total volume of 25 μl containing 50 mM Tris-HCl (pH 7.5), 50 mM NaCl, 2 mM $MnCl_2$, 1 mM DTT, 10% glycerol, 20 units of RNase inhibitor (Promega), cold ribonucleotide mixture (0.5 mM each ATP, CTP, and GTP, and 5 μM UTP), and 10 μCi of [α-$^{32}$P] UTP (3,000 Ci/mmol; Amersham Biosciences). The reaction mixture was incubated with 500 ng of RNA templates, which were prepared as described in Example 6, for 2 hrs at 32° C. After reaction, the RNA products were extracted and analyzed by electrophoresis on 8 M urea-5% polyacrylamide gels as described in Example 4. The results revealed that SARS-CoV nsp12 could copy the 3'(+)UTR339ΔA and 3'(+)UTR339+17A RNA templates, which represent parts of SARS-CoV genome, as demonstrated by incorporation of radioactive ribonucleotides into RNA products (FIG. 12). This result also indicated that both the 3'(+)UTR339ΔA RNA lacking poly(A) tail and the 3'(+)UTR339+17A RNA templates, regardless of the presence or absence of poly(A) tail, can be used by the nsp12 for de novo initiation of RNA synthesis.

Example 8

Preparation of SARS-CoV 3'(+)UTR151ΔA and 3'(−)UTR121 RNA Templates

SARS-CoV genome-derived 3'(+)UTR151ΔA and 3'(−)UTR121 RNA, which were used as RNA templates for RdRp activity test in Example 9 below, were prepared by in vitro transcription using T7 RNA polymerase as described in Example 6. The 3'NUTR151ΔA RNA consisting of 151 nucleotides of the 3'-end of SARS-CoV genome, with no poly(A) tail, was in vitro transcribed using the DNA template amplified by PCR with F4 primer and R4 primer. The DNA template for the synthesis of 3'(−)UTR121 RNA was reverse-transcribed using the R5 primer and amplified by PCR with the F5 and R5 primers. The PCR product was used as a template for the synthesis of 121 nucleotides negative strand RNA complimentary to the 5'(+)UTR of SARS-CoV genome by in vitro transcription.

F4 primer:

(SEQ ID NO: 9)
5'-<u>TAATACGACTCACTATAGG</u> ACCACATTTTCATCGAGGCC-3'

(SEQ ID NO: 10)
F5 primer: 5'-ATATTAGGTTTTACCTAC-3'

R5 primer:

(SEQ ID NO: 11)
5'-<u>TAATACGACTCACTATAGG</u> TAGGTGCACTAGGCATGC-3'

In the above primer, the underlined nucleotides are a T7 promoter sequence for transcription, and complimentary sequences to SARS-CoV genome are indicated in bold, capital letters.

Example 9

Analysis of the RNA Synthesis Ability of SARS-CoV nsp12 to Use SARS-CoV Genome-Derived 3'(+)UTR151ΔA and 3'(−)UTR121 RNAs as Templates

RdRp assays were performed with SARS-CoV 3'(+) UTR151ΔA and 3'(−)UTR121 RNA templates prepared as in Example 8 by the methods described in Example 7, and the RdRp products were subjected to denaturing polyacrylamide gel electrophoresis. The results showed that the nsp12 can use both 3'(+)UTR151ΔA and 3'(−)UTR121 RNAs as templates, as demonstrated by incorporation of radioactive substrates into the RNA products. In vitro synthesis of positive strand RNAs by the nsp12 was more efficient than that of negative strand RNA (FIG. 13). This result is consistent with the notion that a greater amount of positive strand RNAs are synthesized than minus strand RNA during viral replication in the cells infected with positive strand RNA viruses. Furthermore, we were able to confirm that the nsp12 requires manganese ion for RdRp activity.

---

The invention claimed is:

1. A recombinant severe acute respiratory syndrome coronavirus (SARS-CoV) nsp12 having the amino acid sequence of SEQ ID NO:1, in which nine amino acids are deleted from the N-terminus and amino acid sequences comprising several histidine residues are fused to the N-terminus.

2. The recombinant SARS-CoV nsp12 according to claim 1 that is expressed by the expression vector pTrcSARSnsp12.

3. A composition for screening inhibitors against RNA-dependent RNA polymerase (RdRp), comprising the recombinant SARS-CoV nsp12 of claim 1, $MnCl_2$, and NTP (nucleoside triphosphate).

4. The composition according to claim 3, wherein the recombinant SARS-CoV nsp12 is expressed by the expression vector pTrcSARSnsp 12.

5. The composition according to claim 3, wherein the NTP includes ATP, GTP, CTP or UTP, which is labeled with a marker probe.

6. A method of screening for inhibitors of RdRp, comprising the following steps:
 a) incubating a candidate compound with the composition according to claim 3; and
 b) determining whether the candidate compound promotes or inhibits an RNA synthesis activity of SARS-CoV nsp12.

7. The method of claim 6, wherein the step b) comprises measuring whether an RNA labeled with a marker nucleotide is synthesized or not.

* * * * *

SEQUENCE LISTING

```
<160> NUMBER OF SEQ ID NOS: 11

<210> SEQ ID NO 1
<211> LENGTH: 936
<212> TYPE: PRT
<213> ORGANISM: Artificial Sequence
<220> FEATURE:
<223> OTHER INFORMATION: Recombinant SARS-CoV nsp12

<400> SEQUENCE: 1

Met Gly Gly Ser His His His His His Gly Met Ala Arg Val Cys
 1               5                   10                  15

Gly Val Ser Ala Ala Arg Leu Thr Pro Cys Gly Thr Gly Thr Ser Thr
                20                  25                  30

Asp Val Val Tyr Arg Ala Phe Asp Ile Tyr Asn Glu Lys Val Ala Gly
            35                  40                  45

Phe Ala Lys Phe Leu Lys Thr Asn Cys Cys Arg Phe Gln Glu Lys Asp
        50                  55                  60

Glu Gly Asn Leu Leu Asp Ser Tyr Phe Val Val Lys Arg His Thr
 65                 70                  75                  80

Met Ser Asn Tyr Gln His Glu Glu Thr Ile Tyr Asn Leu Val Lys Asp
                85                  90                  95

Cys Pro Ala Val Ala Val His Asp Phe Phe Lys Phe Arg Val Asp Gly
                100                 105                 110

Asp Met Val Pro His Ile Ser Arg Gln Arg Leu Thr Lys Tyr Thr Met
            115                 120                 125

Ala Asp Leu Val Tyr Ala Leu Arg His Phe Asp Glu Gly Asn Cys Asp
        130                 135                 140

Thr Leu Lys Glu Ile Leu Val Thr Tyr Asn Cys Cys Asp Asp Asp Tyr
145                 150                 155                 160

Phe Asn Lys Lys Asp Trp Tyr Asp Phe Val Glu Asn Pro Asp Ile Leu
                165                 170                 175

Arg Val Tyr Ala Asn Leu Gly Glu Arg Val Arg Gln Ser Leu Leu Lys
            180                 185                 190

Thr Val Gln Phe Cys Asp Ala Met Arg Asp Ala Gly Ile Val Gly Val
        195                 200                 205

Leu Thr Leu Asp Asn Gln Asp Leu Asn Gly Asn Trp Tyr Asp Phe Gly
    210                 215                 220

Asp Phe Val Gln Val Ala Pro Gly Cys Gly Val Pro Ile Val Asp Ser
225                 230                 235                 240

Tyr Tyr Ser Leu Leu Met Pro Ile Leu Thr Leu Thr Arg Ala Leu Ala
                245                 250                 255

Ala Glu Ser His Met Asp Ala Asp Leu Ala Lys Pro Leu Ile Lys Trp
            260                 265                 270
```

```
Asp Leu Leu Lys Tyr Asp Phe Thr Glu Glu Arg Leu Cys Leu Phe Asp
        275                 280                 285

Arg Tyr Phe Lys Tyr Trp Asp Gln Thr Tyr His Pro Asn Cys Ile Asn
        290                 295                 300

Cys Leu Asp Asp Arg Cys Ile Leu His Cys Ala Asn Phe Asn Val Leu
305                 310                 315                 320

Phe Ser Thr Val Phe Pro Pro Thr Ser Phe Gly Pro Leu Val Arg Lys
                325                 330                 335

Ile Phe Val Asp Gly Val Pro Phe Val Val Ser Thr Gly Tyr His Phe
                340                 345                 350

Arg Glu Leu Gly Val Val His Asn Gln Asp Val Asn Leu His Ser Ser
        355                 360                 365

Arg Leu Ser Phe Lys Glu Leu Leu Val Tyr Ala Ala Asp Pro Ala Met
        370                 375                 380

His Ala Ala Ser Gly Asn Leu Leu Leu Asp Lys Arg Thr Thr Cys Phe
385                 390                 395                 400

Ser Val Ala Ala Leu Thr Asn Asn Val Ala Phe Gln Thr Val Lys Pro
                405                 410                 415

Gly Asn Phe Asn Lys Asp Phe Tyr Asp Phe Ala Val Ser Lys Gly Phe
                420                 425                 430

Phe Lys Glu Gly Ser Ser Val Glu Leu Lys His Phe Phe Phe Ala Gln
        435                 440                 445

Asp Gly Asn Ala Ala Ile Ser Asp Tyr Asp Tyr Arg Tyr Arg Asn Leu
        450                 455                 460

Pro Thr Met Cys Asp Ile Arg Gln Leu Leu Phe Val Val Glu Val Val
465                 470                 475                 480

Asp Lys Tyr Phe Asp Cys Tyr Asp Gly Gly Cys Ile Asn Ala Asn Gln
                485                 490                 495

Val Ile Val Asn Asn Leu Asp Lys Ser Ala Gly Phe Pro Phe Asn Lys
                500                 505                 510

Trp Gly Lys Ala Arg Leu Tyr Tyr Asp Ser Met Ser Tyr Glu Asp Gln
        515                 520                 525

Asp Ala Leu Phe Ala Tyr Thr Lys Arg Asn Val Ile Pro Thr Ile Thr
        530                 535                 540

Gln Met Asn Leu Lys Tyr Ala Ile Ser Ala Lys Asn Arg Ala Arg Thr
545                 550                 555                 560

Val Ala Gly Val Ser Ile Cys Ser Thr Met Thr Asn Arg Gln Phe His
                565                 570                 575

Gln Lys Leu Leu Lys Ser Ile Ala Ala Thr Arg Gly Ala Thr Val Val
        580                 585                 590

Ile Gly Thr Ser Lys Phe Tyr Gly Gly Trp His Asn Met Leu Lys Thr
        595                 600                 605

Val Tyr Ser Asp Val Glu Thr Pro His Leu Met Gly Trp Asp Tyr Pro
        610                 615                 620

Lys Cys Asp Arg Ala Met Pro Asn Met Leu Arg Ile Met Ala Ser Leu
625                 630                 635                 640

Val Leu Ala Arg Lys His Asn Thr Cys Cys Asn Leu Ser His Arg Phe
                645                 650                 655

Tyr Arg Leu Ala Asn Glu Cys Ala Gln Val Leu Ser Glu Met Val Met
                660                 665                 670

Cys Gly Gly Ser Leu Tyr Val Lys Pro Gly Gly Thr Ser Ser Gly Asp
        675                 680                 685

Ala Thr Thr Ala Tyr Ala Asn Ser Val Phe Asn Ile Cys Gln Ala Val
        690                 695                 700
```

-continued

```
Thr Ala Asn Val Asn Ala Leu Leu Ser Thr Asp Gly Asn Lys Ile Ala
705                 710                 715                 720

Asp Lys Tyr Val Arg Asn Leu Gln His Arg Leu Tyr Glu Cys Leu Tyr
            725                 730                 735

Arg Asn Arg Asp Val Asp His Glu Phe Val Asp Glu Phe Tyr Ala Tyr
        740                 745                 750

Leu Arg Lys His Phe Ser Met Met Ile Leu Ser Ala Asp Ala Val Val
    755                 760                 765

Cys Tyr Asn Ser Asn Tyr Ala Ala Gln Gly Leu Val Ala Ser Ile Lys
770                 775                 780

Asn Phe Lys Ala Val Leu Tyr Tyr Gln Asn Asn Val Phe Met Ser Glu
785                 790                 795                 800

Ala Lys Cys Trp Thr Glu Thr Asp Leu Thr Lys Gly Pro His Glu Phe
            805                 810                 815

Cys Ser Gln His Thr Met Leu Val Lys Gln Gly Asp Asp Tyr Val Tyr
        820                 825                 830

Leu Pro Tyr Pro Asp Pro Ser Arg Ile Leu Gly Ala Gly Cys Phe Val
    835                 840                 845

Asp Asp Ile Val Lys Thr Asp Gly Thr Leu Met Ile Glu Arg Phe Val
850                 855                 860

Ser Leu Ala Ile Asp Ala Tyr Pro Leu Thr Lys His Pro Asn Gln Glu
865                 870                 875                 880

Tyr Ala Asp Val Phe His Leu Tyr Leu Gln Tyr Ile Arg Lys Leu His
            885                 890                 895

Asp Glu Leu Thr Gly His Met Leu Asp Met Tyr Ser Val Met Leu Thr
        900                 905                 910

Asn Asp Asn Thr Ser Arg Tyr Trp Glu Pro Glu Phe Tyr Glu Ala Met
    915                 920                 925

Tyr Thr Pro His Thr Val Leu Gln
930                 935

<210> SEQ ID NO 2
<211> LENGTH: 932
<212> TYPE: PRT
<213> ORGANISM: severe acute respiratory syndrome coronavirus

<400> SEQUENCE: 2

Ser Ala Asp Ala Ser Thr Phe Phe Lys Arg Val Cys Gly Val Ser Ala
1               5                   10                  15

Ala Arg Leu Thr Pro Cys Gly Thr Gly Thr Ser Thr Asp Val Val Tyr
            20                  25                  30

Arg Ala Phe Asp Ile Tyr Asn Glu Lys Val Ala Gly Phe Ala Lys Phe
        35                  40                  45

Leu Lys Thr Asn Cys Cys Arg Phe Gln Glu Lys Asp Glu Glu Gly Asn
    50                  55                  60

Leu Leu Asp Ser Tyr Phe Val Val Lys Arg His Thr Met Ser Asn Tyr
65                  70                  75                  80

Gln His Glu Glu Thr Ile Tyr Asn Leu Val Lys Asp Cys Pro Ala Val
            85                  90                  95

Ala Val His Asp Phe Phe Lys Phe Arg Val Asp Gly Asp Met Val Pro
        100                 105                 110

His Ile Ser Arg Gln Arg Leu Thr Lys Tyr Thr Met Ala Asp Leu Val
    115                 120                 125

Tyr Ala Leu Arg His Phe Asp Glu Gly Asn Cys Asp Thr Leu Lys Glu
130                 135                 140
```

```
Ile Leu Val Thr Tyr Asn Cys Cys Asp Asp Tyr Phe Asn Lys Lys
145                 150                 155                 160

Asp Trp Tyr Asp Phe Val Glu Asn Pro Asp Ile Leu Arg Val Tyr Ala
            165                 170                 175

Asn Leu Gly Glu Arg Val Arg Gln Ser Leu Leu Lys Thr Val Gln Phe
            180                 185                 190

Cys Asp Ala Met Arg Asp Ala Gly Ile Val Gly Val Leu Thr Leu Asp
            195                 200                 205

Asn Gln Asp Leu Asn Gly Asn Trp Tyr Asp Phe Gly Asp Phe Val Gln
210                 215                 220

Val Ala Pro Gly Cys Gly Val Pro Ile Val Asp Ser Tyr Tyr Ser Leu
225                 230                 235                 240

Leu Met Pro Ile Leu Thr Leu Thr Arg Ala Leu Ala Ala Glu Ser His
                245                 250                 255

Met Asp Ala Asp Leu Ala Lys Pro Leu Ile Lys Trp Asp Leu Leu Lys
            260                 265                 270

Tyr Asp Phe Thr Glu Glu Arg Leu Cys Leu Phe Asp Arg Tyr Phe Lys
            275                 280                 285

Tyr Trp Asp Gln Thr Tyr His Pro Asn Cys Ile Asn Cys Leu Asp Asp
290                 295                 300

Arg Cys Ile Leu His Cys Ala Asn Phe Asn Val Leu Phe Ser Thr Val
305                 310                 315                 320

Phe Pro Pro Thr Ser Phe Gly Pro Leu Val Arg Lys Ile Phe Val Asp
                325                 330                 335

Gly Val Pro Phe Val Val Ser Thr Gly Tyr His Phe Arg Glu Leu Gly
            340                 345                 350

Val Val His Asn Gln Asp Val Asn Leu His Ser Ser Arg Leu Ser Phe
            355                 360                 365

Lys Glu Leu Leu Val Tyr Ala Ala Asp Pro Ala Met His Ala Ala Ser
370                 375                 380

Gly Asn Leu Leu Leu Asp Lys Arg Thr Thr Cys Phe Ser Val Ala Ala
385                 390                 395                 400

Leu Thr Asn Asn Val Ala Phe Gln Thr Val Lys Pro Gly Asn Phe Asn
                405                 410                 415

Lys Asp Phe Tyr Asp Phe Ala Val Ser Lys Gly Phe Phe Lys Glu Gly
            420                 425                 430

Ser Ser Val Glu Leu Lys His Phe Phe Phe Ala Gln Asp Gly Asn Ala
            435                 440                 445

Ala Ile Ser Asp Tyr Asp Tyr Tyr Arg Tyr Asn Leu Pro Thr Met Cys
450                 455                 460

Asp Ile Arg Gln Leu Leu Phe Val Glu Val Val Asp Lys Tyr Phe
465                 470                 475                 480

Asp Cys Tyr Asp Gly Gly Cys Ile Asn Ala Asn Gln Val Ile Val Asn
            485                 490                 495

Asn Leu Asp Lys Ser Ala Gly Phe Pro Phe Asn Lys Trp Gly Lys Ala
            500                 505                 510

Arg Leu Tyr Tyr Asp Ser Met Ser Tyr Glu Asp Gln Asp Ala Leu Phe
            515                 520                 525

Ala Tyr Thr Lys Arg Asn Val Ile Pro Thr Ile Thr Gln Met Asn Leu
            530                 535                 540

Lys Tyr Ala Ile Ser Ala Lys Asn Arg Ala Arg Thr Val Ala Gly Val
545                 550                 555                 560
```

Ser Ile Cys Ser Thr Met Thr Asn Arg Gln Phe His Gln Lys Leu Leu
            565                 570                 575

Lys Ser Ile Ala Ala Thr Arg Gly Ala Thr Val Val Ile Gly Thr Ser
            580                 585                 590

Lys Phe Tyr Gly Gly Trp His Asn Met Leu Lys Thr Val Tyr Ser Asp
            595                 600                 605

Val Glu Thr Pro His Leu Met Gly Trp Asp Tyr Pro Lys Cys Asp Arg
    610                 615                 620

Ala Met Pro Asn Met Leu Arg Ile Met Ala Ser Leu Val Leu Ala Arg
625                 630                 635                 640

Lys His Asn Thr Cys Cys Asn Leu Ser His Arg Phe Tyr Arg Leu Ala
                645                 650                 655

Asn Glu Cys Ala Gln Val Leu Ser Glu Met Val Met Cys Gly Gly Ser
                660                 665                 670

Leu Tyr Val Lys Pro Gly Gly Thr Ser Ser Gly Asp Ala Thr Thr Ala
            675                 680                 685

Tyr Ala Asn Ser Val Phe Asn Ile Cys Gln Ala Val Thr Ala Asn Val
            690                 695                 700

Asn Ala Leu Leu Ser Thr Asp Gly Asn Lys Ile Ala Asp Lys Tyr Val
705                 710                 715                 720

Arg Asn Leu Gln His Arg Leu Tyr Glu Cys Leu Tyr Arg Asn Arg Asp
                725                 730                 735

Val Asp His Glu Phe Val Asp Glu Phe Tyr Ala Tyr Leu Arg Lys His
            740                 745                 750

Phe Ser Met Met Ile Leu Ser Asp Asp Ala Val Val Cys Tyr Asn Ser
            755                 760                 765

Asn Tyr Ala Ala Gln Gly Leu Val Ala Ser Ile Lys Asn Phe Lys Ala
770                 775                 780

Val Leu Tyr Tyr Gln Asn Asn Val Phe Met Ser Glu Ala Lys Cys Trp
785                 790                 795                 800

Thr Glu Thr Asp Leu Thr Lys Gly Pro His Glu Phe Cys Ser Gln His
                805                 810                 815

Thr Met Leu Val Lys Gln Gly Asp Asp Tyr Val Tyr Leu Pro Tyr Pro
            820                 825                 830

Asp Pro Ser Arg Ile Leu Gly Ala Gly Cys Phe Val Asp Asp Ile Val
            835                 840                 845

Lys Thr Asp Gly Thr Leu Met Ile Glu Arg Phe Val Ser Leu Ala Ile
850                 855                 860

Asp Ala Tyr Pro Leu Thr Lys His Pro Asn Gln Glu Tyr Ala Asp Val
865                 870                 875                 880

Phe His Leu Tyr Leu Gln Tyr Ile Arg Lys Leu His Asp Glu Leu Thr
                885                 890                 895

Gly His Met Leu Asp Met Tyr Ser Val Met Leu Thr Asn Asp Asn Thr
            900                 905                 910

Ser Arg Tyr Trp Glu Pro Glu Phe Tyr Glu Ala Met Tyr Thr Pro His
            915                 920                 925

Thr Val Leu Gln
    930

<210> SEQ ID NO 3
<211> LENGTH: 2799
<212> TYPE: DNA
<213> ORGANISM: Artificial Sequence
<220> FEATURE:
<223> OTHER INFORMATION: cDNA of SARS-CoV nsp12

<400> SEQUENCE: 3

```
tctgcggatg catcaacgtt ttttaaacgg gtttgcggtg taagtgcagc ccgtcttaca      60
ccgtgcggca caggcactag tactgatgtc gtctacaggg cttttgatat ttacaacgaa     120
aaagttgctg gttttgcaaa gttcctaaaa actaattgct gtcgcttcca ggagaaggat     180
gaggaaggca atttattaga ctcttacttt gtagttaaga ggcatactat gtctaactac     240
caacatgaag agactattta aacttggtt aaagattgtc cagcggttgc tgtccatgac      300
tttttcaagt ttagagtaga tggtgacatg gtaccacata tatcacgtca gcgtctaact     360
aaatacacaa tggctgattt agtctatgct ctacgtcatt ttgatgaggg taattgtgat     420
acattaaaag aaatactcgt cacatacaat tgctgtgatg atgattattt caataagaag     480
gattggtatg acttcgtaga gaatcctgac atcttacgcg tatatgctaa cttaggtgag     540
cgtgtacgcc aatcattatt aaagactgta caattctgcg atgctatgcg tgatgcaggc     600
attgtaggcg tactgacatt agataatcag gatcttaatg ggaactggta cgatttcggt     660
gatttcgtac aagtagcacc aggctgcgga gttcctattg tggattcata ttactcattg     720
ctgatgccca tcctcacttt gactagggca ttggctgctg agtcccatat ggatgctgat     780
ctcgcaaaac cacttattaa gtgggatttg ctgaaatatg attttacgga agagagactt     840
tgtctcttcg accgttattt taaatattgg gaccagacat accatcccaa ttgtattaac     900
tgtttggatg ataggtgtat ccttcattgt gcaaacttta atgtgttatt ttctactgtg     960
tttccaccta caagttttgg accactagta agaaaaatat ttgtagatgg tgttcctttt    1020
gttgtttcaa ctggatacca ttttcgtgag ttaggagtcg tacataatca ggatgtaaac    1080
ttacatagct cgcgtctcag tttcaaggaa cttttagtgt atgctgctga tccagctatg    1140
catgcagctt ctggcaattt attgctagat aaacgcacta catgctttc agtagctgca    1200
ctaacaaaca atgttgcttt tcaaactgtc aaacccggta attttaataa agacttttat    1260
gactttgctg tgtctaaagg ttttctttaag gaaggaagtt ctgttgaact aaaacacttc    1320
ttctttgctc aggatggcaa cgctgctatc agtgattatg actattatcg ttataatctg    1380
ccaacaatgt gtgatatcag acaactccta ttcgtagttg aagttgttga taaatacttt    1440
gattgttacg atggtggctg tattaatgcc aaccaagtaa tcgttaacaa tctggataaa    1500
tcagctggtt tcccatttaa taaatggggt aaggctagac tttattatga ctcaatgagt    1560
tatgaggatc aagatgcact tttcgcgtat actaagcgta atgtcatccc tactataact    1620
caaatgaatc ttaagtatgc cattagtgca aagaatagag ctcgcaccgt agctggtgtc    1680
tctatctgta gtactatgac aaatagacag tttcatcaga aattattgaa gtcaatagcc    1740
gccactagag gagctactgt ggtaattgga acaagcaagt tttacggtgg ctggcataat    1800
atgttaaaaa ctgtttacag tgatgtagaa actccacacc ttatgggttg ggattatcca    1860
aaatgtgaca gagccatgcc taacatgctt aggataatgg cctctcttgt tcttgctcgc    1920
aaacataaca cttgctgtaa cttatcacac cgtttctaca ggttagctaa cgagtgtgcg    1980
caagtattaa gtgagatggt catgtgtggc ggctcactat atgttaaacc aggtggaaca    2040
tcatccggtg atgctacaac tgcttatgct aatagtgtct ttaacatttg tcaagctgtt    2100
acagccaatg taaatgcact tctttcaact gatggtaata agatagctga caagtatgtc    2160
cgcaatctac aacacaggct ctatgagtgt ctctatagaa atagggatgt tgatcatgaa    2220
ttcgtggatg agttttacgc ttacctgcgt aaacatttct ccatgatgat tctttctgat    2280
gatgccgttg tgtgctataa cagtaactat gcggctcaag gttagtagc tagcattaag    2340
```

-continued

```
aactttaagg cagttcttta ttatcaaaat aatgtgttca tgtctgaggc aaaatgttgg    2400
actgagactg accttactaa aggacctcac gaattttgct cacagcatac aatgctagtt    2460
aaacaaggag atgattacgt gtacctgcct tacccagatc catcaagaat attaggcgca    2520
ggctgttttg tcgatgatat tgtcaaaaca gatggtacac ttatgattga aaggttcgtg    2580
tcactggcta ttgatgctta cccacttaca aaacatccta atcaggagta tgctgatgtc    2640
tttcacttgt atttacaata cattagaaag ttacatgatg agcttactgg ccacatgttg    2700
gacatgtatt ccgtaatgct aactaatgat aacacctcac ggtactggga acctgagttt    2760
tatgaggcta tgtacacacc acatacagtc ttgcagtag                          2799
```

<210> SEQ ID NO 4
<211> LENGTH: 28
<212> TYPE: DNA
<213> ORGANISM: Artificial Sequence
<220> FEATURE:
<223> OTHER INFORMATION: F1 primer

<400> SEQUENCE: 4
gctctagagt ttgcggtgta agtgcagc                                        28

<210> SEQ ID NO 5
<211> LENGTH: 28
<212> TYPE: DNA
<213> ORGANISM: Artificial Sequence
<220> FEATURE:
<223> OTHER INFORMATION: R1 primer

<400> SEQUENCE: 5
cgggatccta ctgcaagact gtatgtgg                                        28

<210> SEQ ID NO 6
<211> LENGTH: 38
<212> TYPE: DNA
<213> ORGANISM: Artificial Sequence
<220> FEATURE:
<223> OTHER INFORMATION: F3 primer

<400> SEQUENCE: 6
taatacgact cactatagga cactcatgat gaccacac                              38

<210> SEQ ID NO 7
<211> LENGTH: 24
<212> TYPE: DNA
<213> ORGANISM: Artificial Sequence
<220> FEATURE:
<223> OTHER INFORMATION: R3 primer

<400> SEQUENCE: 7 ggtctcttttt tttttttttt tttt                                            24

<210> SEQ ID NO 8
<211> LENGTH: 21
<212> TYPE: DNA
<213> ORGANISM: Artificial Sequence
<220> FEATURE:
<223> OTHER INFORMATION: R4 primer

<400> SEQUENCE: 8
gtccattctc ctaagaagct a                                                21

<210> SEQ ID NO 9
<211> LENGTH: 39
<212> TYPE: DNA

-continued

```
<213> ORGANISM: Artificial Sequence
<220> FEATURE:
<223> OTHER INFORMATION: F4 primer

<400> SEQUENCE: 9
taatacgact cactatagga ccacattttc atcgaggcc                    39

<210> SEQ ID NO 10
<211> LENGTH: 19
<212> TYPE: DNA
<213> ORGANISM: Artificial Sequence
<220> FEATURE:
<223> OTHER INFORMATION: F5 primer

<400> SEQUENCE: 10
atattaggtt tttacctac                                          19

<210> SEQ ID NO 11
<211> LENGTH: 37
<212> TYPE: DNA
<213> ORGANISM: Artificial Sequence
<220> FEATURE:
<223> OTHER INFORMATION: R5 primer

<400> SEQUENCE: 11
taatacgact cactataggt aggtgcacta ggcatgc                      37
```